(12) United States Patent
Humayun et al.

(10) Patent No.: US 7,831,309 B1
(45) Date of Patent: Nov. 9, 2010

(54) IMPLANTS BASED ON BIPOLAR METAL OXIDE SEMICONDUCTOR (MOS) ELECTRONICS

(75) Inventors: Mark Humayun, Glendale, CA (US); Howard Phillips, Millerton, OK (US)

(73) Assignee: University of Southern California, Los Angeles, CA (US)

( * ) Notice: Subject to any disclaimer, the term of this patent is extended or adjusted under 35 U.S.C. 154(b) by 0 days.

(21) Appl. No.: 11/951,955

(22) Filed: Dec. 6, 2007

Related U.S. Application Data

(60) Provisional application No. 60/868,907, filed on Dec. 6, 2006.

(51) Int. Cl.
*A61N 1/00* (2006.01)
(52) U.S. Cl. ...................................... 607/54
(58) Field of Classification Search ............ 607/2, 607/53–54, 152, 141; 623/6.63
See application file for complete search history.

(56) References Cited

U.S. PATENT DOCUMENTS

| | | | |
|---|---|---|---|
| 5,045,686 A * | 9/1991 | Iwanami et al. .......... 250/208.1 |
| 5,109,844 A | 5/1992 | de Juan et al. |
| 5,312,439 A * | 5/1994 | Loeb ............................ 607/2 |
| 5,935,155 A | 8/1999 | Humayun et al. |
| 5,944,747 A | 8/1999 | Greenberg et al. |
| 6,719,750 B2 | 4/2004 | Varner et al. |
| 6,800,076 B2 | 10/2004 | Humayun |
| 6,970,745 B2 | 11/2005 | Scribner |
| 7,103,416 B2 | 9/2006 | Ok et al. |
| 7,131,945 B2 | 11/2006 | Fink et al. |
| 7,217,263 B2 | 5/2007 | Humayun et al. |
| 7,228,181 B2 | 6/2007 | Greenberg et al. |
| 7,252,006 B2 | 8/2007 | Tai et al. |
| 2002/0002362 A1 | 1/2002 | Humayun et al. |
| 2002/0026176 A1 | 2/2002 | Varner et al. |
| 2002/0091421 A1 * | 7/2002 | Greenberg et al. ............ 607/54 |
| 2002/0095193 A1 | 7/2002 | Ok et al. |
| 2002/0121281 A1 | 9/2002 | Humayun |
| 2003/0022374 A1 | 1/2003 | Greenbaum et al. |
| 2003/0097165 A1 | 5/2003 | Krulevitch et al. |
| 2003/0176898 A1 * | 9/2003 | Gross et al. .................... 607/54 |
| 2003/0187491 A1 | 10/2003 | Greenberg et al. |
| 2004/0106966 A1 | 6/2004 | Scribner et al. |
| 2004/0116794 A1 | 6/2004 | Fink et al. |
| 2004/0133155 A1 | 7/2004 | Varner et al. |
| 2004/0172100 A1 | 9/2004 | Humayun et al. |
| 2004/0236389 A1 | 11/2004 | Fink et al. |
| 2005/0033272 A1 | 2/2005 | Humayun |
| 2005/0059956 A1 | 3/2005 | Varner et al. |
| 2005/0208457 A1 | 9/2005 | Fink et al. |
| 2005/0268722 A1 | 12/2005 | Tai et al. |
| 2005/0277802 A1 | 12/2005 | Larsen et al. |
| 2006/0003090 A1 | 1/2006 | Rodger et al. |

(Continued)

FOREIGN PATENT DOCUMENTS

WO    WO03/090166    10/2003

*Primary Examiner*—Mark W Bockelman
*Assistant Examiner*—Elizabeth K So
(74) *Attorney, Agent, or Firm*—Fish & Richardson P.C.

(57) ABSTRACT

Intraocular and periocular implantation devices based on one or more implantation electronic chips for implantation within the eye to include a bipolar MOS circuit that is DC biased at or near a natural electrical ground potential of the eye. Described examples include retinal prosthesis devices and techniques that use bipolar MOS electronics.

14 Claims, 4 Drawing Sheets

U.S. PATENT DOCUMENTS

| | | |
|---|---|---|
| 2006/0111605 A1 | 5/2006 | Larsen et al. |
| 2006/0121639 A1 | 6/2006 | Tai et al. |
| 2006/0173511 A1 | 8/2006 | Greenberg et al. |
| 2006/0190058 A1 | 8/2006 | Greenberg et al. |
| 2006/0200097 A1 | 9/2006 | Humayun et al. |
| 2006/0235485 A1 | 10/2006 | Ok et al. |
| 2006/0247664 A1 | 11/2006 | Meng et al. |
| 2006/0247754 A1 | 11/2006 | Greenberg et al. |
| 2006/0253172 A1 | 11/2006 | Greenberg et al. |
| 2006/0259112 A1 | 11/2006 | Greenberg et al. |
| 2006/0282128 A1 | 12/2006 | Tai et al. |
| 2006/0282130 A1 | 12/2006 | Roy et al. |
| 2007/0049987 A1 | 3/2007 | Greenberg et al. |
| 2007/0055089 A1 | 3/2007 | Larsen et al. |
| 2007/0112263 A1 | 5/2007 | Fink et al. |
| 2007/0123766 A1 | 5/2007 | Whalen et al. |
| 2007/0142878 A1 | 6/2007 | Krulevitch et al. |
| 2007/0187238 A1 | 8/2007 | Whalen et al. |
| 2007/0191909 A1 | 8/2007 | Ameri et al. |
| 2007/0191911 A1 | 8/2007 | Greenberg et al. |
| 2007/0244367 A1 | 10/2007 | Caffey et al. |
| 2007/0259420 A1 | 11/2007 | Greenbaum et al. |

* cited by examiner

IMPLANTS BASED ON BIPOLAR METAL OXIDE SEMICONDUCTOR (MOS) ELECTRONICS

PRIORITY CLAIM AND RELATED APPLICATIONS

This application claims the benefit of U.S. Provisional Application No. 60/868,907 entitled "High-Reliability Inneroccular Prosthesis (IOC) Design" and filed on Dec. 6, 2006, which is incorporated by reference as part of the specification of this application.

Other prior patent applications related to this applications are (1) U.S. Provisional Application No. 60/623,731 entitled "Technology Disclosure High-reliability Inneroccular Prosthesis (IOC) Design" and filed on Oct. 28, 2004; and (2) U.S. Provisional Application No. 60/748,487 entitled "Technology Disclosure High-reliability Inneroccular Prosthesis (IOC) Design" and filed on Dec. 7, 2005.

TECHNICAL FIELD

This application relates to medical implantation devices and techniques including intraocular and periocular prosthesis apparatus and techniques.

BACKGROUND

The natural photoreceptors in an eye may degenerate due to various factors such as injury, illness, aging and others. A retinal prosthetic system can be designed to partially or fully restore the vision of an eye by using an electrode array attached to the retina to provide image-carrying electrode pulses to stimulate the natural vision nerve cells attached to the retina. The pulses from the natural vision nerve cells are transmitted to the brain to construct an image.

Such a retinal prosthetic system can be designed in various configurations. For example, a retinal prosthetic system can include a camera worn by a patient to capture images, an image processing and electronic control unit to generate electrical pulses based on each captured image, and a two-dimensional electrode array attached to the retina that applies the electrical pulses to the retina.

The above retinal prosthetic system is an example of various intraocular and periocular implantation devices and systems.

SUMMARY

This application describes examples and implementations of intraocular and periocular implantation devices based on one or more implantation electronic chips for implantation within the eye to include a bipolar metal oxide semiconductor (MOS) circuit that is direct current (DC) biased at or near a natural electrical ground potential of the eye.

Described examples include retinal prosthesis devices and techniques that use bipolar MOS electronics.

In one aspect, a retinal prosthesis devices includes an electrode array comprising an array of electrodes and configured for implantation on a retina of an eye to output electrical pulses to optical nerves of the eye; and an implantation electronic chip for implantation within the eye comprising bipolar MOS shift registers that are DC biased at or near a natural electrical ground potential of the eye. The implantation electronic chip is responsive to a modulated image-carrying electrical signal to produce an array of electrical currents to the array of electrodes of the electrode array to cause the output of the electrical pulses to optical nerves of the eye. This device includes an electrical connection connected between the implantation electronic chip and the electrode array.

In another aspect, a retinal prosthesis device includes an electrode array comprising an array of electrodes and configured for implantation on a retina of an eye to output electrical pulses to optical nerves of the eye and an implantation electronic chip for implantation in the eye comprising a demodulator circuit that receives and processes a time-division multiplexed (TDM) image-carrying electrical signal, a demultiplexer circuit to process the output from the demodulator circuit to produce an array of pixel signals representing an image carried in the modulated image-carrying electrical signal, and a current generator circuit responsive to the array of pixel signals to produce an array of electrical currents to the array of electrodes of the electrode array to cause the output of the electrical pulses to optical nerves of the eye. The demultiplexer circuit comprises bipolar MOS shift registers that are DC biased at or near a natural electrical ground potential of the eye. This device also includes an electrical connection connected between the implantation electronic chip and the electrode array.

These and other implementations and examples of visual prosthesis apparatus and techniques are described in greater detail in the drawings, the detailed description and the claims.

DETAILED DESCRIPTION

This application describes examples and implementations of intraocular and periocular implantation devices based on bipolar MOS electronics, including retinal and other visual prosthesis devices, intraocular and periocular drug delivery devices, and intraocular pressure sensors. The use of bipolar MOS electronics in such implants can avoid various adverse effects such as field effects encountered by CMOS chips in saline environments.

Figure 1:
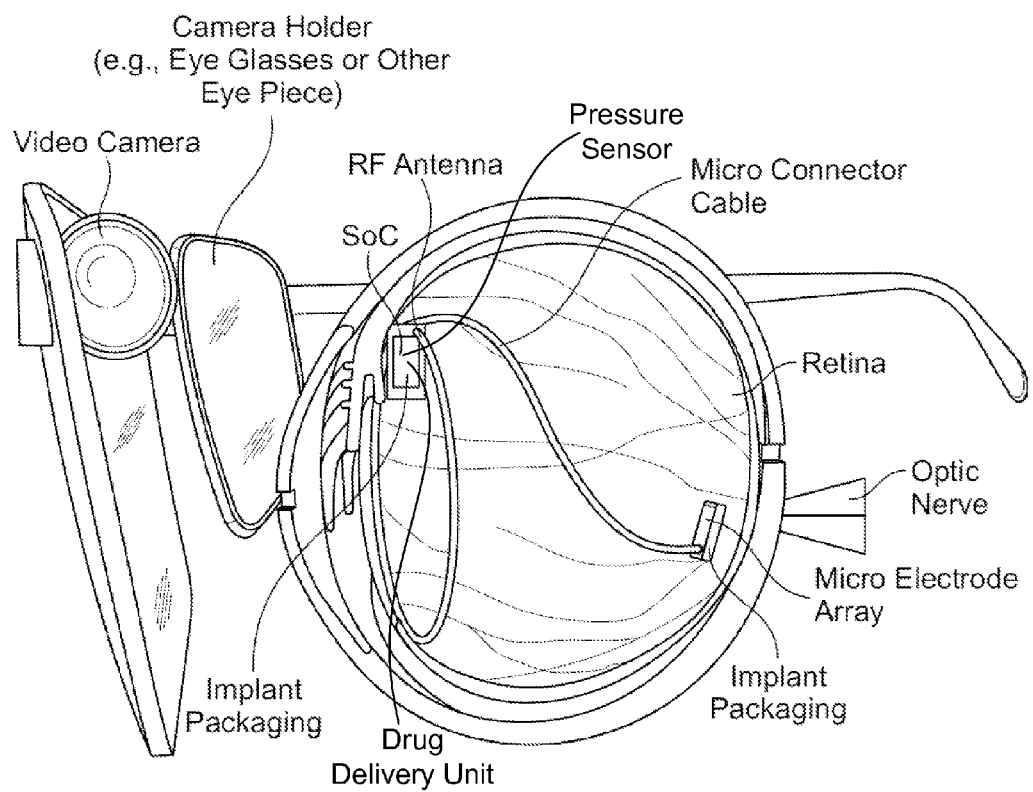
FIG. 1 shows an example of a retinal prosthetic system installed in an eye.

FIG. 1 shows an example of a retinal prosthetic system installed in an eye. A video camera is engaged to a camera holder which can be a pair of eye glasses or other eye piece worn by the patient. This system includes implanted components such as packaged electronics labeled as "SoC" that receives image signals from the video camera either wirelessly via RF transmitter and transceiver coils or other means, a micro connector cable that conduct the output form the SoC electronics and a multi-channel electrode array attached to the retina to receive the output from the SoC electronics and to apply stimulus electronic pulses to the optical nerves. The implanted electronics can perform power recovery, management of data reception and transmission, digital processing, and analog output of stimulus currents to the electrode array. Examples of an intra-ocular prosthesis (IOP) is described to provide reduced technical risk associated with sodium-induced threshold voltage shift of metal oxide semiconductor (MOS) devices. One way of doing this is to use time-division multiplexing (TDM) with bipolar IC technology.

Figure 2A:
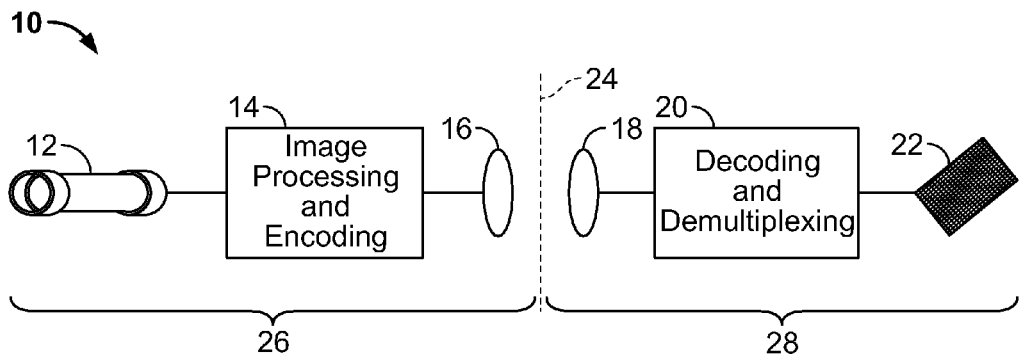
FIGS. 2A, 2B and 2C show a specific implementation of the retinal prosthetic system in FIG. 1.
Figure 2B:
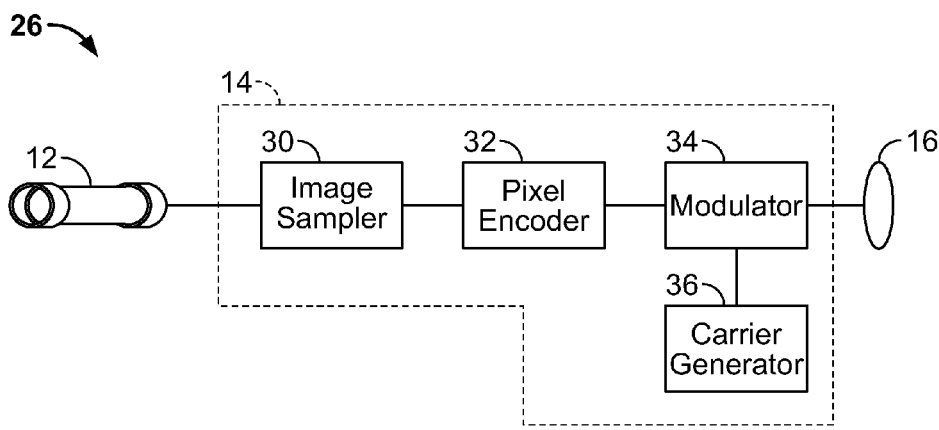
Figure 2C:
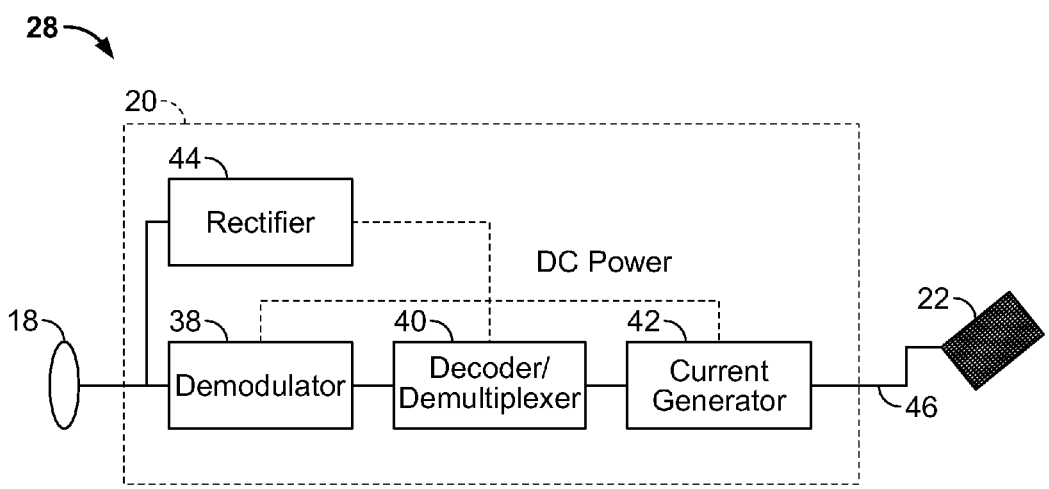

FIGS. 2A, 2B and 2C show a specific implementation of the retinal prosthetic system in FIG. 1. This system includes an image acquiring and transmitting portion and a receiving and retina stimulating portion. The acquiring portion includes a camera for generating a visual signal output representative of an acquired image. The stimulating portion includes an electrode array adapted to be operatively attached to the user's retina. The visual signal output is used to modulate a radio frequency (RF) carrier signal which is applied to a primary coil. A secondary coil receives the RF signal which is then demodulated to recover the visual signal output for driving the electrode array to electrically stimulate retinal tissue. In use, the acquiring and transmitting portion is mounted outside of the eye (extracellular) and the receiving and stimulating portion is primarily mounted in the eye (intraocular). The components of the intraocular portion are powered from energy extracted from the transmitted visual signal.

FIG. 2A depicts the visual prosthesis 10 which includes an image capturing element, such as a charge coupled device (CCD) camera 12, whose output is processed and encoded in circuit block 14. This processed and encoded captured real image signal is then coupled via primary coil 16 to a secondary coil 18. For example, the real image signal can be transmitted as a modulated radio frequency (RF) carrier signal. The secondary coil 18 receives the real image signal and applies an output signal to the signal processing circuit block 20. This circuit block 20 decodes and demultiplexes the applied signal and then communicates an apparent image signal to an electrode array 22 which stimulates the retinal cells to produce phosphenes in a pattern to simulate vision. The dashed line 24 in FIG. 2A is included to functionally separate the image acquiring and transmitting portion 26 from the image receiving and stimulating portion 28 of the visual prosthesis 10. The dashed line 24 may or may not indicate the physical separation of extracellular and intraocular components as will be described more fully hereinafter with reference to FIGS. 3A and 3B.

The image acquiring and transmitting portion 26 of the visual prosthesis 10 is illustrated in greater detail in FIG. 2B which shows the output of camera 12 coupled to an image sampler circuit 30 whose output is passed to a pixel encoder 32. The output of encoder 32 is passed to a signal modulator 34 which modulates a radio frequency carrier signal generated by the carrier generator 36. This RF signal is then applied to the primary coil 16.

In one implementation, the encoding scheme can be optimized for the target image resolution which can be primarily determined by the size of the implanted electrode array. The encoded information typically includes such parameters as the magnitude, timing, and sequence of the stimulation pulses which are generated by the electrode array to simulate the image through retinal stimulation.

The RF signal applied to primary coil 16 is received by the secondary coil 18 of the stimulating portion 28 as illustrated in greater detail in FIG. 2C. The secondary coil 18 output is passed to the demodulator 38 where the RF carrier signal is removed and the encoded image signal recovered. The encoded image signal is then passed to a decoder/demultiplexer 40 which in turn outputs the image information to a current generator 42 which drives the individual electrodes of the electrode array 22 via conductor 46. The electric power for components of the image receiving and stimulating portion 28 is derived from the energy contained in the coupled RF signal through rectifier 44.

Figure 3A:
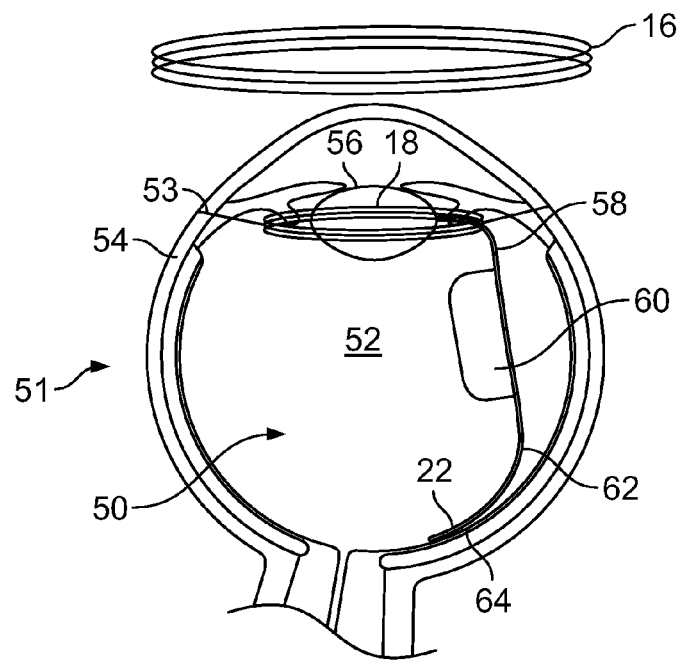
FIGS. 3A and 3B shows two exemplary configurations of the intraocular part of the system in FIGS. 2A, 2B and 2C where the control electronics inside the eye is based on a bipolar MOS technology.
Figure 4:
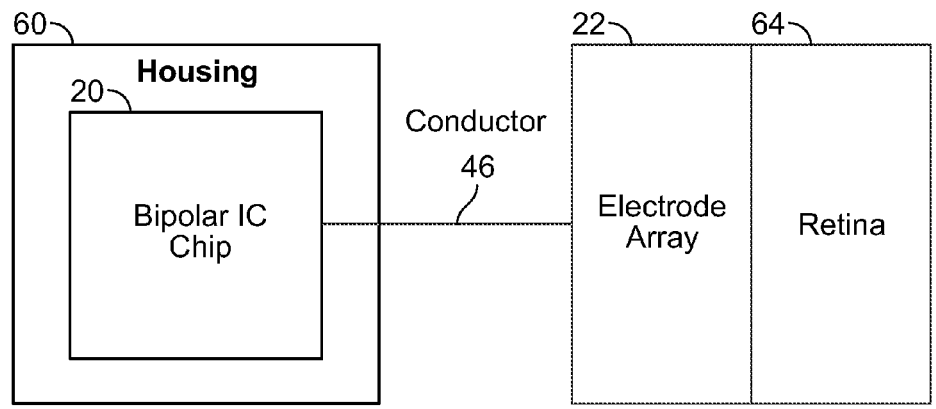
FIG. 4 shows components inside the eye including the bipolar MOS IC chip.

FIG. 3A depicts a first example of the implanted parts of the system in which all of the components of the receiving and retina stimulating portion 28 are implanted in the vitreous chamber 50 of a user's eye 51. The chamber 50 is filled with the vitreous body 52 which comprises a clear colorless transparent jelly. As depicted in FIG. 4, the secondary coil 18 is fixed, e.g., by suture 53 to the adjacent sclera wall 54, just behind the lens 56. The secondary coil 18 is preferably axially aligned with the extracellular primary coil 16 and the optic axis of the eye. The respective coils are preferably mounted so that their planes are oriented substantially parallel to one another to achieve good signal coupling. The secondary coil 18 is physically and electrically connected 58 to signal processing circuitry 20 mounted in housing 60 which preferably comprises a metal can but which can constitute any coating or envelope capable of providing protection from the deleterious effects of salt water. The circuitry 20 in housing 60 is connected via conductor 62 to a flexible electrode array 22 physically and electrically contacting the user's retina 64. The secondary coil 18, housing 60 and electrode array 22 are all mounted in the vitreous body 52 in good thermal contact therewith. Thus, the vitreous body acts as a heat sink to cool the coil and electronic circuitry enabling the system to more efficiently utilize the signal energy derived from primary coil 16.

The housing 60 can be implemented as a hermetically sealed container made of a metal or other electrically conductive material having perpendicular width, depth, and length dimensions. In order to minimize eddy current induction into the housing wall, it is preferable to orient the housing with its smallest dimensions oriented parallel to the plane of coil 18 and preferably displaced from the coil axis.

Figure 3B:
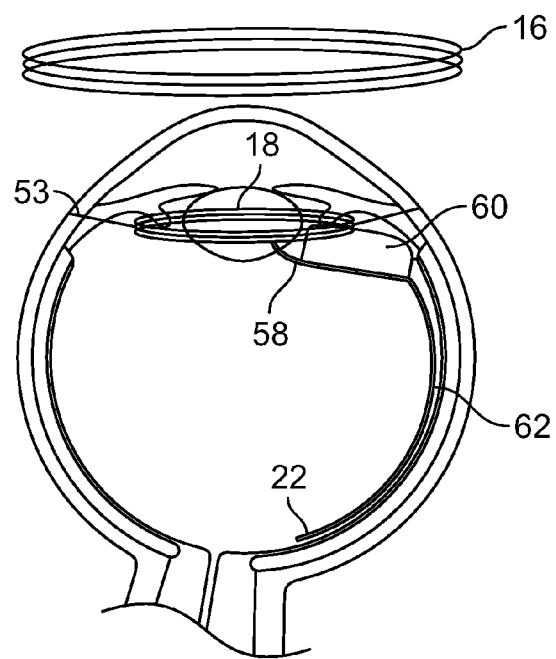

FIG. 3B shows another implementation that differs from FIG. 3A in that housing 60 is placed to the side of coil 18 where it is fixed to the adjacent sclera wall, rather than hanging in the vitreous body as shown in FIG. 3A. The arrangement of FIG. 3B can offer greater mechanical stability and robustness.

FIG. 4 shows components inside the eye including the bipolar MOS IC chip. The use bipolar MOS IC design can reduce technical risks associated with sodium-induced threshold voltage shift of MOS devices. For example, the time-division multiplexing (TDM) with bipolar IC technology can be used to achieve this. As a specific implementation example, a low-risk circuit design can use the established 64-bit 74LS164 shift register (SR) from Texas Instrument, which has been in the marketplace for 30 years and is well-proven as a digital SSI (Small-Scale Integration) building-block IC. The data sheet description of the shift register is posted on the WWW at http://focus.ti.com/lit/ds/symlink/sn74ls164.pdf.

Figure 5:
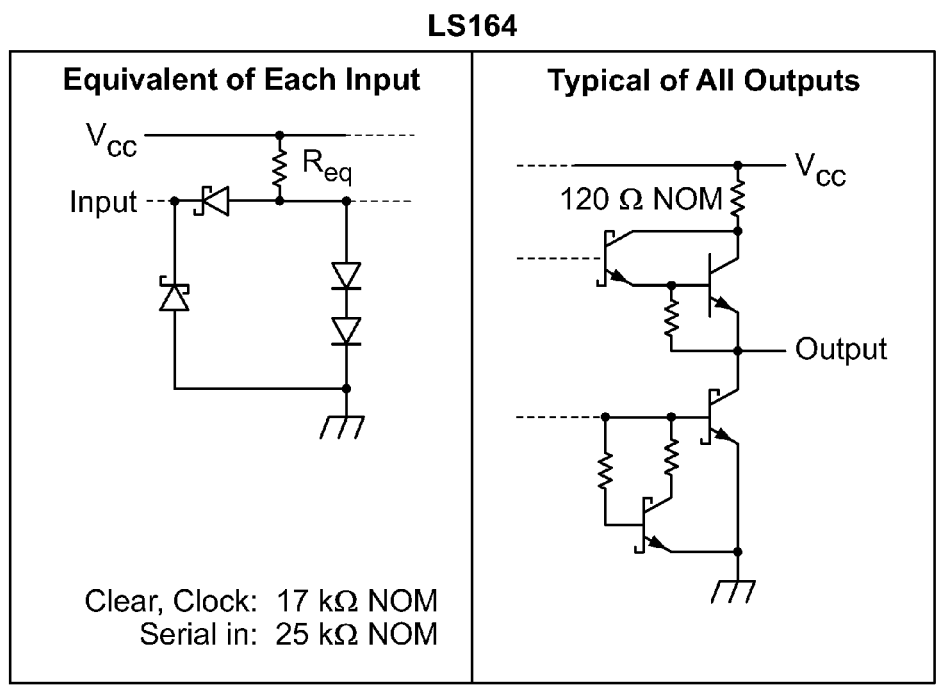
FIG. 5 shows one example of a commercial bipolar MOS shift register that can be used in the bipolar MOS IC chip in FIG. 4.

FIG. 5 shows the equivalent input and output of the 74LS164 shift register. This shift register can be used in the decoder/demultiplexer 40 of the electronics 20 in FIG. 2C. The following is from the data sheet for 74LS164 shift register:

These 8-bit shift registers feature gated serial inputs and an asynchronous clear. The gated serial inputs (A and B) permit complete control over incoming data as a low at either input inhibits entry of the new data and resets the first flip-flop to the low level at the next clock pulse. A high-level input enables the other input which will then determine the state of the first flip-flop. Data at the serial inputs may be changed while the clock is high or low, but only information meeting the setup-time requirements will be entered. Clocking occurs on the low-to-high-level transition of the clock input. All inputs are diode-clamped to minimize transmission-line effects.

It is desirable to attempt to explore the limits of bipolar technology. Ultimately, the number of stimulating electrodes in the electrode array 22 in FIG. 4, also referred to as the number of pixels, will likely depend on the power consumption per pixel. The inside of the eye can be heated to only about 1 degree centigrade due to heat dissipation of the electronics.

Referring back to FIG. 2C, one embodiment uses a MINIMUM number of leads or wires going into the eye. Preferably, these wires are not biased at a DC voltage which differs from the human body potential. Routing such a DC voltage into the body can be problematic in part because of the corrosion that happens when the DC voltage different from the body ground potential is applied to wires entering the body. Even with good insulation, pinholes in the insulation have been shown to be a significant engineering/biological problem.

To have a minimum power and a minimum number of wires into the eye where the shift register is located, the following features can be implemented.

1. The Electrical and Data Part of the System

The 64-bit shift register can be used as a "commutator" form of TDM. As a specific example, this 64-bit SR can be operated at a clock frequency of about 3.84 KHz (low frequency, lower power; meets our frame-rate requirements). If a larger pixel array is used, a 1024-bit array would require a clock frequency of only about 61.44 KHz. The SR can also be operated at the lowest Vcc possible when shifting data into the SR to save power.

The operation of the SR can begin by resetting the SR. This reset operation will be done by serial loading the SR with logic-0 into all bits. This will make the bonding pads "low" for all bits. This completes the "reset" without having a dedicated wire for this purpose. The CLR input to the SR will not be used for reset. When the SR is loaded with the right data, we will stop the clock. With the clock stopped, the stimulating pulse is applied to the Vcc lead. This higher-voltage pulse appears at the outputs of each of the SR bits that have been set to a logic-1 level. This positive pulse can be about 7 to 10 volts (beyond the Vcc spec of the SR) for about a millisecond. The pulse will go to all bits that have been set to a logic-1 and the pulse will be delivered to the bonding pads. The bonding pads are the stimulating electrodes.

After the stimulating pulse is delivered, the Vcc will be returned to a lower voltage for normal operation of the SR. A data stream of all logic-0 data will be shifted into all bits of the SR. This is the reset which does NOT require an extra wire going into the eye, to the SR, for reset.

Next, the above sequence repeats by using a serial data stream to set each of the 64 pixels to either a logic-1 or a logic-0.

2. Minimum Number of Wires Going into the Eye

Two schemes can be used to achieve the minimum number of wires into the eye. One scheme requires only 4 wires for any number of pixels. The other scheme requires only 6 wires for any number of pixels.

The 4 wire design—This design requires D, D', GND and CLK signals. The CLK signal has no d.c. component but the D, D' and GND wires have some D.C. component depending on a number of factors such as the ratio of the number of "1" bits to the number of "0" bits. The GND wire carries some D.C. current, but is at "human body ground" potential and therefore has minimal (but some) corrosion potential. The D and D' wires have some d.c. component, but there are frequent high-to-low transitions (this wire is not positive with respect to ground for more than a fraction of a millisecond in normal use). In this scheme, there is no Vcc wire, since the Vcc D.C. power is developed from rectification of the D, D' and CLK signals. This can be done on-chip if there are 3 diodes available using simple half-wave rectification. Several methods have been considered for achieving this:

An alternate scheme is the use of diodes on a test structure (already existing) on the wafer that can be included in the chip which will contain eight 8-bit SRs.

An alternate scheme is a 2-chip hybrid design—one chip for the diodes and one chip for the SRs.

An alternate scheme is a custom design, with fully-integrated diodes and SRs (a more compact [smaller area] chip design).

In this design, there is no Vcc power supply ripple, and no need for a power supply filter. The power-supply capacitor has been completely designed out. In fact, such a capacitor is not desired, since the stimulation pulse will arrive through the Vcc line to the SR and then on to the selected output pads (stimulation electrodes).

The 6-wire design—This design is an "all A.C. design" and will control an unlimited number of pixels in a TDM application. Each channel requires 2 wires, and there are a total of only 3 channels of connection going into the eye. Each channel can be driven by an isolation transformer—an accepted method of improving safety when any electrical system is connected to the body. The three channels are CLK, D and D'. There is no d.c. component on any of these channels. There is no Vcc wire going into the eye, because each channel is full-wave rectified and diode coupled to the Vcc node. There is no GND wire going into the eye because the only GND node is at "human body ground" potential. There are two design options:

In the case where the stimulation electrodes (SR output pads) are Ta (covered by tantalum pentoxide), there is no D.C. ground in the system other than the reference potential for Vcc, and the entire IOP is A.C. coupled to the retina.

In the case where the stimulation electrodes are electrically conductive (low resistance connection), the GND connection is made with the retina through all stimulation electrodes that are grounded (not pulsed by the stimulation pulse).

3. The Chip Layout Part of the Scheme

In one implementation, the wafer containing the SRs is not diced as usual (one SR per chip). Instead, for a pixel array of 8×8, the chip can contain 8 of the SRs. Each SR would be a 74LS164. The bonding pad locations can be located at various locations in a period array or a non-periodic array and software mapping can be used to load data into the SR even if the output bonding pads are not in a nice periodic array.

4. Special Wafer-Fab Processing

Wafers suitable for implementing the present techniques can be various wafers and, notably, can be wafers that do NOT meet specs for TI's standard products. These wafers can be from wafer lots that might represent yield loss. In particular, we would BENEFIT from having wafers that HIGHER than spec value for the resistors, and higher voltage handling capability. The higher resistance provides a benefit of lower power (we don't need the high speed capability of the 74LS164). The higher voltage handling capability will be needed because we plan to pulse the Vcc wire with higher-than-spec voltage, using 1 millisecond pulses about 30 times per second (max rate).

Special processing of the IC may be used, with the special processing steps being ADDED at the end of the standard 74LS164 wafer fab process. Our starting point would be FINISHED wafers, using the standard TI bipolar fab process for the 74LS164 device, but BEFORE the dicing step.

In fabrication, two new masks may be used: one for metal patterning and one for oxide removal to provide access to bonding pads following SiO2 passivation of the extra metal layer. These masks would have a very forgiving registration requirement, and alignment would be the least-critical of all the wafer-fab photoprocessing steps.

5. Special Wafer Fab Steps to Create a 64-Bit Shift Register

Some or all of the following processing steps can be used to create a serial in/64 bit parallel output SR on a single chip:

1. Additional metal interconnect layer—An added layer of TANTALUM or TITANIUM metal interconnect would be needed. The Ta or Ti will form an oxide that will passivate any exposed metal interconnect within the eye, and minimize corrosion. Aluminum metal cannot withstand the effects of corrosion when exposed to the vitreous humor (salt water) in the eye.

2. The layer of TANTALUM or TITANIUM metal interconnect would connect all the Vcc leads together for the 8 SRs, and all the grounds, and the CLK pads and the CLR pads, so that there would be only one input to the 64-bit array for Vcc; one GND, etc. The CLR node would be connected to Vcc by this metal layer, since we require no externally-applied reset command.

3. On each SR, the A and B inputs would be tied together, and those inputs (for the first cascade-connected SR) would be the ONLY data input to the entire array.

4. The 8 SRs would be cascade connected. The SRs would be connected to create a serial in/64-bit parallel output shift register.

5. Next, passivating SiO2 would be applied as normal, and it would be patterned so that oxide removal would reveal the SELECTED bonding pads. Access would be provided to all output bonding pads, the single input, the single ground, and the single Vcc. [Actually, good engineering practice might be to provide access to TWO of each of these so that later wirebonding would offer some option to the wirebonding operator.] These pads would be selected from pads on the outside of the chip, for the same reasons that wirebonding pads are usually placed on the outside of any bar layout.

A sintering step may be performed, to clear any unwanted oxide between conducting nodes and ensure low resistance (high conductivity) between Si, Al and Ta layers.

The output pads can be capacitively coupled to the retinal tissue during stimulation. This can conserve charge balance and prevent tissue damage. The output coupling capacitor will consist of the Ta pad, the tantalum pentoxide capacitor dielectric and the retinal tissue (the other capacitor plate) which functions as a complex-impedance electrical load during electrical stimulation.)

When the Ta metal is replaced with a metal that tends to not oxidize (or forms a conducting oxide), the output pads (stimulation electrodes) would be D.C. coupled to the retinal tissue.

After the above process, the wafers are wafer-probe tested, marked and diced. Next, the wires are attached to the chips and the electrical-driver/test electronics, electrical testing, cleaning and preparation for implantation may be performed.

6. Clock Rate Calculations

The clock rate can be set at 30 frames/sec minimum, to prevent flicker being sensed by the human eye.

(Pixel count)*(frame rate)=data rate required for data only. Multiply this number by 2 to allow for clearing the array before loading data into the SR.

$$\text{Clock freq} = (\text{Pixel count}) * (\text{frame rate}) * (30 \text{ frames/sec})$$

This 8×8 design requires a minimum clock rate=64*30*2=3.84 KHz.

A 16×16 array device would require a min clock rate of 4*3.84=15.360 KHz.

A 32×32 array device would require a min clock rate of 4*15.360=61.440 KHz.

These clock frequencies are SO FAR BELOW the minimum clock frequency capability of a 74LS164 SR device that our design should look for ways to trade off frequency to achieve lower power dissipation.

7. Tantalum for the Stimulating Electrode

Tantalum metal may be preferred in various devices because tantalum metal is strong, ductile, highly conductive, biocompatible, inexpensive and readily drawn into wire of any desired dimension. It spontaneously forms a native oxide.

An implant device may use tantalum and tantalum pentoxide as a complete system for the conveyance of electrical stimulation pulses from stimulus-forming circuitry to the tissue to be stimulated.

A preferred application is a prosthesis. Such prosthesis comprises a multiplicity of electrode contacts made from tantalum, connected to stimulus pulse-forming electronic circuitry.

This may advantageously eliminate the need for coupling capacitors without the usual danger of having d.c. current flow to the saline fluids.

The fabrication is simplified, and the reliability is improved for the electrode array and associated flexible cable connecting the array to the stimulus-forming circuitry.

The electrical implant device may avoid the use of coupling capacitors, yet eliminates the danger of applying DC current to saline fluids/tissue.

Implantable electrodes, or an implantable electrode array, may be used that employs tantalum metal.

An implantable stimulation device wherein tantalum and tantalum pentoxide combine to provide a complete system for the conveyance of electrical stimulation pulses to the saline fluids/tissue to be stimulated.

The described bipolar MOS designs can be used in various arrays of varying array sizes such as an 8×8 pixel array, an 16×16 pixel array, and an 32×32 pixel array with a 1024-bit SR. The power/pixel limitations because of the tissue heating limitations can constrain the use of bipolar SR TDM technology to smaller devices than can be obtained with CMOS.

CMOS circuitry designs may not be suitable for operations when unpackaged (non-hermetically sealed) in the eye (a salt-water-like vitreous humor) which offers the very important reliability threat of sodium contamination and threshold voltage shifts in CMOS transistors. Currently, bipolar devices offer the promise of high reliability for an inner-ocular prosthetic active-electronics device.

While this specification contains many specifics, these should not be construed as limitations on the scope of the invention or of what may be claimed, but rather as descriptions of features specific to particular embodiments of the invention. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Only a few embodiments are disclosed. However, it is understood that variations and enhancements may be made.

What is claimed is:

1. A retinal prosthesis device, comprising:
    an electrode array comprising an array of electrodes and configured for implantation on a retina of an eye to output electrical pulses to optical nerves of the eye;
    an implantation electronic chip for implantation within the eye comprising bipolar metal oxide semiconductor (MOS) shift registers that are direct current (DC) biased at or near a natural electrical ground potential of the eye, the implantation electronic chip responsive to a modulated image-carrying electrical signal to produce an array of electrical currents to the array of electrodes of the electrode array to cause the output of the electrical pulses to optical nerves of the eye; and
    an electrical connection connected between the implantation electronic chip and the electrode array.

2. The device as in claim 1, wherein:
    the implantation electronic chip is configured to operate in a time-division multiplexing configuration.

3. The device as in claim 2, wherein:
    the electrical connection has four conductive wires.

4. The device as in claim 2, wherein:
    the electrical connection has six conductive wires which are free of DC signals.

5. The device as in claim 1, wherein:
    each electrode in the electrode array is made of tantalum.

6. A retinal prosthesis device, comprising:
    an electrode array comprising an array of electrodes and configured for implantation on a retina of an eye to output electrical pulses to optical nerves of the eye;
    an implantation electronic chip for implantation in the eye comprising a demodulator circuit that receives and processes a time-division multiplexed (TDM) image-carrying electrical signal, a demultiplexer circuit to process the output from the demodulator circuit to produce an array of pixel signals representing an image carried in the modulated image-carrying electrical signal, and a current generator circuit responsive to the array of pixel signals to produce an array of electrical currents to the array of electrodes of the electrode array to cause the output of the electrical pulses to optical nerves of the eye, wherein the demultiplexer circuit comprises bipolar metal oxide semiconductor (MOS) shift registers that are direct current (DC) biased at or near a natural electrical ground potential of the eye; and
    an electrical connection connected between the implantation electronic chip and the electrode array.

7. The device as in claim 6, wherein:
    the electrical connection has four conductive wires.

8. The device as in claim 6, wherein:
    the electrical connection has six conductive wires which are free of DC signals.

9. The device as in claim 6, wherein:
    each electrode in the electrode array is made of tantalum.

10. The device as in claim 6, comprising:
    a video camera to capture images;
    an image processing and encoding circuit to produce a TDM signal that carries the captured images from the video camera;
    a first radio frequency (RF) coil that wirelessly transmits the TDM signal; and
    a second RF coil that receives the TDM signal from the first RF coil and directs the received TMD signal into the implantation electronic chip.

11. An intraocular implantation device, comprising:
    an implantation electronic chip for implantation within an eye comprising a bipolar metal oxide semiconductor (MOS) circuit that is direct current (DC) biased at or near a natural electrical ground potential of the eye.

12. The device as in claim 11, wherein the device includes a drug delivery unit to deliver a drug into the eye.

13. The device as in claim 11, wherein the device includes an intraocular pressure sensor that senses a pressure.

14. A periocular implantation device, comprising:
    an implantation electronic chip for implantation within an eye comprising a bipolar metal oxide semiconductor (MOS) circuit that is direct current (DC) biased at or near a natural electrical ground potential of the eye.

* * * * *